US009452935B2

(12) United States Patent
Kuhl

(10) Patent No.: US 9,452,935 B2
(45) Date of Patent: Sep. 27, 2016

(54) PROCESS AND SYSTEM FOR CONVERSION OF CARBON DIOXIDE TO CARBON MONOXIDE

(71) Applicant: CCP TECHNOLOGY GMBH, Munich (DE)

(72) Inventor: Olaf Kuhl, Greifswald (DE)

(73) Assignee: CCP Technology GmbH (DE)

( * ) Notice: Subject to any disclaimer, the term of this patent is extended or adjusted under 35 U.S.C. 154(b) by 2 days.

(21) Appl. No.: 14/232,934

(22) PCT Filed: Dec. 20, 2012

(86) PCT No.: PCT/EP2012/005309
§ 371 (c)(1),
(2) Date: Jun. 24, 2014

(87) PCT Pub. No.: WO2013/091878
PCT Pub. Date: Jun. 27, 2013

(65) Prior Publication Data
US 2015/0291433 A1    Oct. 15, 2015

(30) Foreign Application Priority Data

Dec. 20, 2011   (DE) .................. 10 2011 122 562
May 4, 2012     (DE) .................. 10 2012 008 933
Aug. 2, 2012    (DE) .................. 10 2012 015 314

(51) Int. Cl.
*C07C 27/00* (2006.01)
*C01B 31/18* (2006.01)
(Continued)

(52) U.S. Cl.
CPC ............ *C01B 31/18* (2013.01); *B01J 19/0013* (2013.01); *B01J 19/126* (2013.01); *B01J 19/245* (2013.01); *C01B 3/24* (2013.01); *C01B 31/02* (2013.01); *C07C 1/041* (2013.01); *C07C 1/0485* (2013.01); *C10G 2/32* (2013.01); *C10G 2/34* (2013.01); *C10J 3/00* (2013.01); *C10K 3/06* (2013.01);
(Continued)

(58) Field of Classification Search
CPC ................ B01J 2203/0277; B01J 2203/1041; B01J 2203/1058; B01J 2203/1241; C01B 2203/0475; C01B 31/0206; C01B 31/18; C10G 2/30
USPC ........................................ 518/702; 252/373
See application file for complete search history.

(56) References Cited

U.S. PATENT DOCUMENTS 4,040,976 A    8/1977   Greene
4,190,636 A    2/1980   Schmerling et al.
(Continued)

FOREIGN PATENT DOCUMENTS

CA    2770290    2/2011
CA    2829552    9/2012
(Continued)

*Primary Examiner* — Jafar Parsa
(74) *Attorney, Agent, or Firm* — Tarolli, Sundheim, Covell & Tummino LLP

(57) ABSTRACT

A process and an apparatus for converting carbon dioxide $CO_2$ into carbon monoxide CO using hydrocarbons are described. In further embodiments, processes and apparatuses for generating synthesis gas and processes and apparatuses for converting synthesis gas into synthetic functionalized and/or non-functionalized hydrocarbons using $CO_2$ and hydrocarbons are described. The processes and apparatuses are adapted to convert $CO_2$ emitted by industrial processes, and thus the amount of carbon dioxide emitted into the atmosphere may be reduced.

17 Claims, 4 Drawing Sheets

(51) Int. Cl.

| | |
|---|---|
| *C01B 3/24* | (2006.01) |
| *C10J 3/00* | (2006.01) |
| *C10K 3/06* | (2006.01) |
| *C10G 2/00* | (2006.01) |
| *C01B 31/02* | (2006.01) |
| *B01J 19/12* | (2006.01) |
| *C07C 1/04* | (2006.01) |
| *B01J 19/24* | (2006.01) |
| *B01J 19/00* | (2006.01) |

(52) U.S. Cl.
CPC .......... *B01J 2219/00051* (2013.01); *B01J 2219/0898* (2013.01); *B01J 2219/1206* (2013.01); *B01J 2219/24* (2013.01); *C01B 2203/0255* (2013.01); *C01B 2203/0272* (2013.01); *C01B 2203/062* (2013.01); *C01B 2203/0833* (2013.01); *C01B 2203/0861* (2013.01); *C01B 2203/1235* (2013.01); *C10G 2400/04* (2013.01); *C10J 2300/094* (2013.01); *C10J 2300/0943* (2013.01); *C10J 2300/0973* (2013.01); *C10J 2300/1659* (2013.01); *C10J 2300/1884* (2013.01); *Y02P 20/129* (2015.11)

(56) References Cited

U.S. PATENT DOCUMENTS

U.S. PATENT DOCUMENTS

| | | |
|---|---|---|
| 4,353,713 A | 10/1982 | Cheng |
| 5,164,054 A | 11/1992 | Cha et al. |
| 5,767,165 A | 6/1998 | Steinberg et al. |
| 5,989,512 A | 11/1999 | Lynum et al. |
| 2003/0024806 A1 | 2/2003 | Foret |
| 2005/0063900 A1* | 3/2005 | Wang ............. B01J 23/002 423/658.2 |
| 2008/0156630 A1 | 7/2008 | Lee et al. |
| 2011/0209576 A1* | 9/2011 | Roth ............... C10B 49/02 75/330 |
| 2012/0241676 A1 | 9/2012 | Kim et al. |
| 2014/0052831 A1 | 2/2014 | Wijnands et al. |

FOREIGN PATENT DOCUMENTS

| | | |
|---|---|---|
| GB | 873213 | 8/1958 |
| JP | 2008-545603 | 12/2008 |
| JP | 2012-188321 | 10/2012 |
| KR | 10-2011-0013968 | 2/2011 |
| WO | WO 2009/079681 A1 * | 7/2009 |
| WO | 2010/015385 | 2/2010 |

* cited by examiner

PROCESS AND SYSTEM FOR CONVERSION OF CARBON DIOXIDE TO CARBON MONOXIDE

RELATED APPLICATIONS

This application corresponds to PCT/EP2012/005309, filed Dec. 20, 2012, which claims the benefit of German Applications Nos 10 2011 122 562.9, filed Dec. 20, 2011; 10 2012 008 933.3, filed May 4, 2012; and 10 2012 015 314.7, filed Aug. 2, 2012, the subject matter of which is incorporated herein by reference in their entirety.

BACKGROUND OF THE INVENTION

The present invention relates to a method and a plant for generating carbon monoxide from hydrocarbons and $CO_2$.

Large amounts of carbon dioxide ($CO_2$), which is regarded as climate damaging gas, are generated in power generation and other industrial processes. Great efforts are made to avoid generation of carbon dioxide. Furthermore, attempts are made to separate the generated carbon dioxide from flue gases and to store the carbon dioxide. One example is the $CO_2$ storage or Carbon-Capture-to-Storage concept, abbreviated CCS concept, where the $CO_2$ is separated from the flue gases, thereafter compresses and stored in appropriate geological formations. The CCS process is expensive, energy intensive, limited in the storage capacities and is—for various reasons—strongly opposed by the respective population. At least in Germany, the technical and political feasibility seems to have failed.

Another possibility is the use of carbon dioxide as starting material for other industrial processes, i.e. as starting material in the plastics industry for producing polyurethane, as it is done by the Bayer AG in the project CO2RRECT. Regarding the amounts of involved $CO_2$, the use of $CO_2$ as starting material is only a niche application, since the total global production of the end products of such an application is too low to convert a significant amount of the emitted carbon dioxide.

None of these concepts resulted in applications that are able to bind large amounts of carbon dioxide or that are socially acceptable in their implementation.

Synthesis gas, or abbreviated syngas, is a gas mixture containing carbon monoxide and hydrogen that may also contain carbon dioxide. For example, the syngas is generated by gasification of carbon containing fuel to a gaseous product having a certain calorific value. The synthesis gas has approximately 50% of the energy density of natural gas. The synthesis gas may be burned and thus used as a fuel source. The synthesis gas may also be used as an intermediate product in the generation of other chemical products. For example, the synthesis gas may be generated by gasification of coal or waste. In the generation of synthesis gas, carbon may be reacted with water, or a hydrocarbon may be reacted with oxygen. There are commercially available technologies for processing synthesis gas in order to generate industrial gases, fertilisers, chemicals and other chemical products. However, most known technologies (e.g. water-shift-reaction) for the generation and conversion of synthesis gas have the problem that synthesising the required amount of hydrogen causes the generation of a larger amount of surplus $CO_2$ which is finally emitted into the atmosphere as a climate damaging gas. Another known technology for the production of synthesis gas, the partial oxidation of methane according to the equation $2CH_4+O_2 \rightarrow 2CO+4H_2$, is able to reach a maximum ratio of $H_2$:CO of 2.0. However, the disadvantage thereof is the use of pure oxygen that is energy intensively produced.

DD 276 098 A1 describes a more complete material utilisation of natural gas in steam reforming plants. In particular, a process for generating soot from natural gas by means of arc plasma pyrolysis is described among others. Further, U.S. Pat. No. 4,040,976 A describes treatment of a carbonaceous material, especially coal, with carbon dioxide for generating a carbon monoxide gas. In said treatment, the carbon dioxide is first mixed with the carbonaceous material and thereafter is rapidly heated in a reactor together with carbon dioxide at a rate of >500° C./s, and afterwards is rapidly cooled, wherein the heating phase lasts from 0.1 to 50 ms and the entire contact time of the reactants is limited to a time range of 10 ms to 5 s. Furthermore, generating carbon monoxide in a plasma is known from U.S. Pat. No. 4,190,636 A, where a plasma is generated from carbon monoxide, into which solid carbon is introduced. The resulting products are thermally quenched and filtered so as to obtain carbon monoxide.

EP 0 219 163 A2 discloses a method for generating synthesis gas, wherein hydrocarbonaceous material is decomposed into carbon and hydrogen in a first reactor chamber, and wherein the carbon is transferred to a second reactor chamber and reacts with $H_2O$ steam in the second reactor chamber.

GB 873 213 A2 discloses a method for generating synthesis gas, wherein first hydrocarbon is decomposed to carbon by means of a catalyst, and thereafter the catalyst in contact with the carbon is exposed to $CO_2$.

Therefore, a problem to be solved is to provide a method for converting $CO_2$, the method being able to efficiently reduce the amount of carbon dioxide emitted by industrial processes and to enable production of chemical products in demand.

SUMMARY OF THE INVENTION

The invention provides a method for converting carbon dioxide $CO_2$ into carbon monoxide CO comprises decomposing a hydrocarbon containing fluid into carbon and hydrogen by means of introduction of energy that is at least partially provided by heat, whereby the carbon and the hydrogen have a temperature of at least 200° C. after the decomposing step. Subsequently, at least a portion of the carbon generated by the decomposing step is mixed with $CO_2$ gas, wherein the carbon generated by the decomposing step cools down by not more than 50% in ° C. with respect to its temperature after the decomposing step upon mixing with $CO_2$ gas, and wherein at least a portion of the $CO_2$ gas and a portion of the carbon generated by the decomposing step is converted to CO at a temperature of 800 to 1700° C. This method enables, in a simple and efficient way, converting $CO_2$ to CO, wherein at least a portion of the energy required for providing carbon (by decomposing hydrocarbon) is employed in the converting step in form of heat.

This is particularly true, if the decomposing step takes place at a temperature over 1000° C. and the carbon is mixed with the $CO_2$ gas at a temperature of at least 800° C., since in this case no additional heat or only a small amount of additional heat needs to be provided for converting $CO_2$ to CO. Preferably, the heat required to reach the temperature of 800 to 1700° C. (specifically about 1000° C.) for the $CO_2$ conversion is essentially completely provided by the heat that is used for decomposing the hydrocarbon containing fluid. Here, essentially completely means that at least 80%, specifically at least 90% of the required heat originates from the decomposing step.

In one embodiment, the carbon obtained by the decomposing step and the hydrogen obtained by the decomposing step are both jointly mixed with the $CO_2$ gas. Hydrogen does not compromise the conversion and may serve as an additional heat transfer substance. This is particularly advantageous, if the carbon and the hydrogen have a temperature of 1000° C. (a preferred conversion or transformation temperature) or above. In this case, the gas after conversion is not pure CO but a synthesis gas. Alternatively, the carbon obtained by the decomposing step may be separated from the hydrogen obtained by the decomposing step prior to mixing with $CO_2$ gas.

In order to increase the energy efficiency of the method, at least a portion of the heat of at least a portion of the carbon and/or the a portion of hydrogen obtained by the decomposing step may be used to heat the $CO_2$ gas prior to the step of mixing the $CO_2$ gas with the carbon and/or to may be used to heat the process chamber, in which the $CO_2$ gas is mixed with the carbon. In this sense it should be noted that the CO has a temperature of 800 to 1700° C. after conversion and that at least a portion of its heat may be used to preheat the $CO_2$ gas prior to the step of mixing the $CO_2$ gas with carbon. It is also possible that at least part of the heat of at least a portion of the carbon and/or a portion of the hydrogen obtained by the decomposing step and/or a portion of the CO after conversion may be used to generate electricity which may be used as energy carrier for introducing energy for decomposing the hydrocarbon containing fluid.

Preferably, the energy for decomposing the hydrocarbon is primarily introduced via a plasma. This is a particularly direct and thus efficient method to introduce energy. Preferably, the decomposing step is performed in a Kvaerner reactor that enables continuously decomposing a stream of hydrocarbons.

In the method for generating a synthesis gas, at first $CO_2$ is converted or transformed into CO as described above and, subsequently, the CO is mixed with hydrogen. Preferably, the hydrogen originates from decomposing a hydrocarbon containing fluid into carbon and hydrogen by introducing energy that is at least partially performed by heat. Therefore, the decomposing step may provide the carbon and also the hydrogen necessary for the $CO_2$ conversion in one step. In one embodiment, at least a portion of the hydrogen is generated by decomposing a hydrocarbon containing fluid at a temperature below 1000° C., specifically below 600° C., by means of a microwave plasma. Where additional hydrogen (more than the amount that is obtained by the production of the carbon necessary for the $CO_2$ conversion) is required to reach the mixing ratio of a synthesis gas, it is preferred to produce said hydrogen in an energy efficient manner at low temperatures from a hydrocarbon containing fluid. Preferably, the ratio of CO to hydrogen in the synthesis gas is adjusted to a value between 1:1 and 1:3, specifically to a value of 1:2.1.

In the method for generating synthetic functionalised and/or non-functionalised hydrocarbons, at first a synthesis gas is generated as described above, and the synthesis gas is brought into contact with a suitable catalyst in order to cause a conversion of the synthesis gas into synthetic functionalised and/or non-functionalised hydrocarbons, wherein the temperature of the catalyst and/or the synthesis gas is (open loop) controlled or (close loop) regulated to a predefined temperature range. In this way, the synthesis gas may be generated by mixing CO with hydrogen, either before or upon bringing it into contact with the catalyst.

In one embodiment, the conversion of the synthesis gas is performed by a Fischer-Tropsch process, specifically a SMDS process. Alternatively, the conversion of the synthesis gas may be performed by a Bergius-Pier process, a Pier process or a combination of a Pier process with a MtL process (MtL=methanol to liquid). It is the choice of the process, which largely determines the nature of the synthetic functionalised and/or non-functionalised hydrocarbons.

Preferably, the hydrocarbon containing fluid to be decomposed is natural gas, methane, wet gas, heavy oil, or a mixture thereof.

The apparatus for converting carbon dioxide $CO_2$ into carbon monoxide CO comprises a hydrocarbon converter for decomposing a hydrocarbon containing fluid into carbon and hydrogen, wherein the hydrocarbon converter comprises at least one process chamber having at least one inlet for a hydrocarbon containing fluid and at least one outlet for carbon and/or hydrogen and at least one unit for introducing energy into the process chamber, the energy consisting at least partially of heat. Further the apparatus comprises a $CO_2$ converter for converting $CO_2$ into CO, the $CO_2$ converter comprising at least one additional process chamber having at least one inlet for $CO_2$, at least one inlet for at least carbon and at least one outlet, wherein the inlet for at least carbon is directly connected to the at least one outlet of the hydrocarbon converter. Here, the term "directly connected" describes that carbon coming out of the hydrocarbon converter does not cool down by more than 50% of its temperature in ° C., preferably not more than 20%, on its way to the $CO_2$ converter without the utilisation of additional energy to heat up the carbon. A separating unit, which separates the carbon from the hydrogen, may be provided between the location of the decomposing step and the at least one exit of the hydrocarbon converter. This separating unit may form a part of hydrocarbon converter or may be located outside the hydrocarbon converter as a separate unit. A separating unit between the exit of the hydrocarbon converter and the entrance of a C converter does not compromise a direct connection as long as the above condition is met.

Preferably, the at least one unit for introducing energy into the process chamber is constructed in such a way that it is able to at least locally generate temperatures above 1000° C., specifically above 1500° C. In one embodiment, the at least one unit for introducing energy into the process chamber is a plasma unit. Particularly, if the decomposing temperature shall be kept below 1000° C., the at least one unit for introducing energy into the process chamber preferably comprises a microwave plasma unit.

For a particularly simple embodiment of the apparatus, the process chamber of the $CO_2$ converter is formed by an outlet pipe of the hydrocarbon converter which is connected to a supply pipe for $CO_2$ gas.

In one embodiment of the invention, a separation unit for separating the carbon and the hydrogen generated by decomposing is provided in the vicinity of the hydrocarbon converter, and separate outlets from the separation unit are provided for the separated materials, wherein the outlet for carbon is connected to the $CO_2$ converter.

Preferably, the hydrocarbon converter is a Kvaerner reactor that can provide the necessary temperatures for a continuous decomposing of a hydrocarbon containing fluid for long operating periods.

The apparatus for generating synthesis gas comprises an apparatus of the previously described type as well as at least one separate supply pipe for supplying hydrogen into the $CO_2$ converter or a downstream mixing chamber. Such an apparatus enables a simple and efficient generation of a synthesis gas from $CO_2$ and hydrocarbon containing fluid.

In one embodiment, the apparatus for generating synthesis gas comprises at least one additional hydrocarbon converter for decomposing a hydrocarbon containing fluid into carbon and hydrogen. The at least one additional hydrocarbon converter again comprises at least one process chamber having at least one inlet for the hydrocarbon containing fluid, at least one unit for introducing energy into the process chamber, wherein the energy at least partly consists of heat, and a separation unit for separating the carbon and the hydrogen, which were obtained by decomposing, with the separation unit having separate outlets for carbon and hydrogen, wherein the outlet for hydrogen is connected to the separate supply pipe for hydrogen. For reasons of energy efficiency, the at least one additional hydrocarbon converter is preferably of the type that carries out decomposing at temperatures below 1000° C., specifically below 600° C., by means of a microwave plasma.

The apparatus for converting a synthesis gas into synthetic functionalised and/or non-functionalised hydrocarbons comprises an apparatus for generating synthesis gas of the above specified type and a CO converter. The CO converter comprises a process chamber equipped with a catalyst, means for bringing the synthesis gas into contact with the catalyst and a control unit for (open loop) controlling or (close loop) regulating the temperature of the catalyst and/or the synthesis gas to a predetermined temperature. In this way, parts of the apparatus for generating synthesis gas may be integrated into the CO converter, e.g. a mixing chamber for CO and additional hydrogen. In one embodiment, the CO converter comprises a Fischer-Tropsch converter, particularly a SMDS converter. Alternatively, the CO converter may comprise a Bergius-Pier converter, a Pier converter or a combination of a Pier converter and a MtL converter. It is also possible that several CO converters of the same type or of different types are provided in the apparatus.

Preferably, the apparatus comprises a control unit for controlling or regulating the pressure of the synthesis gas inside the CO converter.

BRIEF DESCRIPTION OF THE DRAWINGS

Below, the invention is explained in more detail with reference to certain embodiments and drawings, wherein.

DESCRIPTION OF EMBODIMENTS

Figure 1:
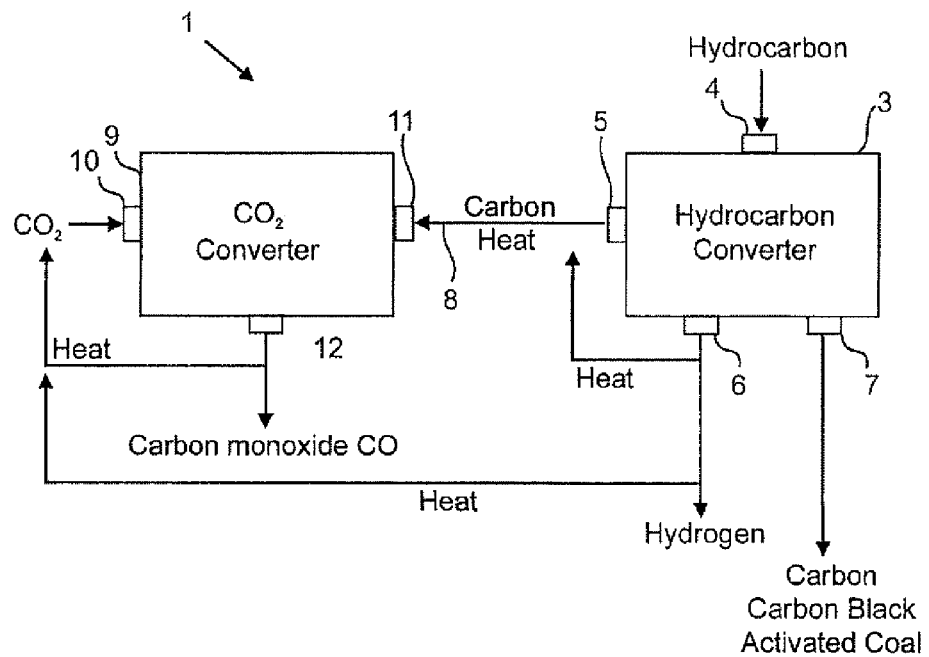
FIG. 1 is a schematic representation of a plant for generating carbon monoxide.

It shall be noted the terms top, bottom, right and left as well as similar terms in the following description relate to the orientations and arrangements, respectively, shown in the figures and are only meant for the description of the embodiments. These terms are not limiting. Further, in the different figures, the same reference numerals are used for describing the same or similar parts.

In the following description, processes and apparatuses are described that handle "hot" materials or carry out "hot" processes. In the context of this description, the expression "hot" shall describe a temperature above 200° C. and preferably above 300° C.

FIG. 1 schematically shows a plant 1 for converting carbon dioxide to carbon monoxide. FIG. 1 also clarifies the basic process steps for converting carbon dioxide to carbon monoxide according to this description.

Plant 1 comprises a hydrocarbon converter 3 that comprises a hydrocarbon inlet 4 and a first carbon outlet 5, an optional hydrogen outlet 6 as well as an optional second carbon outlet 7. Plant 1 for generating carbon monoxide further comprises a $CO_2$ converter 9 having a $CO_2$ inlet 10, a carbon outlet 11 (also referred to as C inlet) and an outlet 12. The hydrocarbon converter 3 and the $CO_2$ converter 9 are arranged such that the carbon outlet 5 of the hydrocarbon converter 3 is connected to the carbon inlet 11 of the $CO_2$ converter 9 via a direct connection 8, wherein the outlet 5 may directly define the carbon inlet 11 of the $CO_2$ converter 9. In this way, carbon may be directly transported from the hydrocarbon converter 3 into the $CO_2$ converter 9.

The hydrocarbon converter 3 is any hydrocarbon converter that can convert or decompose introduced hydrocarbons into carbon and hydrogen. The hydrocarbon converter 3 comprises a process chamber having an inlet for a hydrocarbon containing fluid, at least one unit for introducing decomposing energy into the fluid and at least one outlet. The decomposing energy is provided at least partially by heat, which is for instance provided by a plasma. Nevertheless, the decomposing energy may also be provided by other means and, if decomposing is primarily effected by heat, the fluid should be heated to above 1000° C. and particularly to a temperature above 1500° C.

In the described embodiment, a Kvaerner reactor is used, which provides the required heat by means of a plasma arc and a plasma torch. However, other reactors are known, which operate at lower temperatures, particularly below 1000° C., and introduce additional energy besides heat into the hydrocarbon, e.g. by means of a microwave plasma. As is further explained below, the invention considers both types of reactors (and also those which operate without plasma), in particular also both types of reactors in combination with each other. Hydrocarbon converters operating at a temperature above 1000° C. are referred to as high temperature reactors, whereas those converters operating at temperatures below 1000° C., particularly at temperatures between 200° C. and 1000° C., are referred to as low temperature reactors.

Within the hydrocarbon converter, hydrocarbons ($C_nH_m$) are decomposed into hydrogen and carbon by means of heat and/or a plasma. These hydrocarbons are preferably introduced into the reactor as gases. Hydrocarbons that are liquids under standard conditions may be vaporised prior to introduction into the reactor or they may be introduced as micro-droplets. Both forms are referred to as fluids in the following.

Decomposing of the hydrocarbons should be done, if possible, in the absence of oxygen in order to suppress the formation of carbon oxides or water. Nevertheless, small amounts of oxygen, which might be introduced together with the hydrocarbons, are not detrimental for the process.

The Kvaerner reactor described above decomposes hydrocarbon containing fluids in a plasma burner at high temperatures into pure carbon (for instance as activated coal, carbon black, graphite or industrial soot) and hydrogen and, possibly, impurities. The hydrocarbon containing fluids used as starting material for the hydrocarbon converter 3 are for instance methane, natural gas, biogases, wet gases or heavy oil. However, synthetic functionalised and/or non-functionalised hydrocarbons may also be used as starting material for the hydrocarbon converter 3. After the initial decomposing step, the elements are usually present as a mixture, particularly in form of an aerosol. This mixture may, as described below, be introduced into another process in this form, or the mixture may be separated into its individual elements in a separation unit, which is not shown. In the context of this application, such a separation unit is considered as part of the hydrocarbon converter 3, although the separation unit may be constructed as a separate unit. If no separation unit is provided, the carbon outlet 5 is the only outlet of the hydrocarbon converter 3 and directs a mixture (an aerosol) of carbon and hydrogen directly into the $CO_2$ converter 9. If the separation unit is provided, carbon, which is at least partially separated from hydrogen, may be directed into the hydrocarbon converter 9 using the carbon outlet 5. Separated hydrogen and, possibly, additional carbon may be discharged by means of the optional outlets 6 and 7.

The $CO_2$ converter 9 may be any suitable $CO_2$ converter that can generate carbon monoxide (CO) from carbon (C) and carbon dioxide ($CO_2$). In the embodiment of FIG. 1, the $CO_2$ converter 9 operates according to a part of a known reaction in a blast furnace, wherein said part reaction takes place at temperatures between about 750° C. and 1200° C. without the necessity of a catalyst. Preferably, the $CO_2$ converter operates at a temperature between 800° C. and 1000° C., wherein the heat required to reach that temperature primarily is provided by the exit material of the hydrocarbon converter 3, as will be described below in more detail. In the $CO_2$ converter 9, $CO_2$ is directed over hot carbon or is mixed with hot carbon (and possibly hydrogen) so as to be converted according to the chemical reaction $CO_2+C \rightarrow 2CO$. The $CO_2$ converter 9 operates best at the Boudouard equilibrium and at a temperature of 1000° C. At temperatures of around 800° C., about 94% carbon monoxide will be provided, and at temperatures of around 1000° C., around 99% carbon monoxide will be provided. A further increase in temperature does not result in significant changes.

The operation of plant 1 for converting carbon dioxide into carbon monoxide is described in more detail below, with reference to FIG. 1. In the following, it is assumed that the hydrocarbon converter 3 is a high temperature (HT) reactor of the Kvaerner type. Hydrocarbon containing fluids (specifically in gaseous form) are introduced into the hydrocarbon converter 3 via the hydrocarbon inlet 4. If the hydrocarbon is for instance methane ($CH_4$), then 1 mol carbon and 2 mol hydrogen will be produced from 1 mol methane. The hydrocarbons are decomposed at about 1600° C. in the hydrocarbon converter 3 according to the following reaction equation, wherein the introduced energy is heat that is generated in the plasma by means of electric energy:

$$C_nH_m + \text{Energy} \rightarrow nC + m/2 H_2$$

With appropriate process control, the Kvaerner reactor is capable to convert almost 100% of the hydrocarbons into their components in a continuous operation.

In the following, it is assumed that the carbon and the hydrogen are separated in the hydrocarbon converter 3 and that carbon and hydrogen will be discharged largely separated. However, it is also possible that separation does not occur but carbon and hydrogen will be discharged and introduced into the $CO_2$ converter 9 as a mixture. The hydrogen does not compromise the conversion process in the $CO_2$ converter 9, but may serve as an additional heat transfer substance. The carbon is at least partially directed directly via the carbon outlet 5 into the carbon inlet 11 of the $CO_2$ converter 9. The term "directly" directing from outlet 5 of the hydrocarbon converter 3 to the carbon inlet 11 of the $CO_2$ converter 9 shall include all embodiments wherein the directed materials do not experience a cooling down of more than 50% of the temperature (preferably not more than 80% (annotation of the translator: obviously it was meant to be 20%, i.e. 80% residual energy/temperature—see next paragraph). Since the carbon that exits from the hydrocarbon converter 3 has a high temperature, preferably over 1000° C., the heat energy contained therein may be used to maintain the temperature necessary for the conversion process in the $CO_2$ converter 9, which preferably operates at a temperature of about 1000° C.

The connection 8 between the hydrocarbon converter 3 and the $CO_2$ converter 9 is designed such that the carbon does not cool down much (less than 50%, preferably less than 20% with respect to the temperature) on its way from the hydrocarbon converter 3 to the $CO_2$ converter 9. For instance, the connection 8 may be specially insulated and/or actively heated, wherein the system is preferably not provided with additional heat—i.e. not in addition to the heat introduced in the hydrocarbon converter 3. The hydrogen generated in the hydrocarbon converter 3 also contains heat energy because of the operating temperature in the hydrocarbon converter 3. Therefore, one possibility for heating the connection 8 is to use the heat energy of the hydrogen that exits through the hydrogen outlet 6 to heat the connection 8 between the hydrocarbon converter 3 and the $CO_2$ converter 9 either directly or indirectly via a heat exchanger unit.

In the $CO_2$ converter, $CO_2$, which is introduced through the $CO_2$ inlet 10 of the $CO_2$ converter 9, is directed over hot carbon and/or is mixed with hot carbon. The $CO_2$ converter operates best at the Boudouard equilibrium, which occurs during the reaction of carbon dioxide with hot carbon. The reaction, which is known to the person skilled in the art, depends on pressure and temperature and will not be described in detail. Either the amount of the $CO_2$ or the amount of carbon introduced into the $CO_2$ converter 9 may be (open loop) controlled and/or (close loop) regulated by appropriate means.

$$CO_2 + C \rightarrow 2CO \quad \Delta H = +172.45 \text{ kJ/mol}$$

The $CO_2$ may originate e.g. from a power plant (coal, gas and/or oil operated) or from another industrial process (e.g. steel or cement production) generating appropriate amounts of $CO_2$. Depending on the temperature of the $CO_2$ from the $CO_2$ source, it is advantageous to preheat the $CO_2$ introduced into the $CO_2$ inlet 10 of the $CO_2$ converter 9, as the $CO_2$ converter 9 operates at a temperature between 800 and 1200° C. Preheating of the $CO_2$ may be achieved e.g. by using the heat energy contained in the hot hydrogen either directly or indirectly via a heat exchange unit to preheat the $CO_2$. Preferably, the heat contained in the carbon is sufficient to heat the $CO_2$ to the desired temperature. Only in the case where the heat generated in the hydrocarbon converter 3 is not sufficient to reach the desired conversion temperature of about 1000° C., an optional additional heating unit for heating the $CO_2$ converter 9 or elements contained therein may be provided. Such a unit may also be provided as a preheating unit in the vicinity of a supply line for $CO_2$ or carbon. Such a unit may also be provided only for the start-up phase of the plant in order to bring the $CO_2$ converter 9 or media containing parts of the plant to a starting temperature so that the system can faster reach a desired temperature state. Heating of all media containing parts exclusively via the heat generated in the hydrocarbon converter 3 might take too long in the beginning.

Hot carbon monoxide (CO) having a temperature of about 800 to 1000° C. (depending on the operating temperature of the $CO_2$ converter 9) exits from the $CO_2$ converter 9. The carbon monoxide that exits from the $CO_2$ converter 9 also contains heat energy, which may be used e.g. to preheat the $CO_2$ introduced into the $CO_2$ inlet 10, either directly or indirectly via a heat exchange unit (not shown in FIG. 1).

As mentioned above, the hydrocarbon converter 3 may comprise a second carbon outlet 7 to discharge carbon. The carbon generated in the hydrocarbon converter 3 may be discharged—after a respective separation step (or as a C—$H_2$ mixture)—in different proportions through the first carbon outlet 5 and the second carbon outlet 7. The second carbon outlet 7 is used to discharge a portion of the generated carbon that is not used in the $CO_2$ converter 9 to generate carbon monoxide. The carbon discharged through the second carbon outlet 7 may be discharged as activated carbon, graphite, carbon black or another modification such as carbon cones or carbon discs. Depending on the form and the quality of the discharged carbon, the discharged carbon may be used as raw material for the chemical industry or the electronics industry. Possible applications are for instance the manufacture of semiconductors, the production of tires, inks, toner or similar products. The carbon generated by the hydrocarbon converter 3 is a highly pure raw material that can be processed very well.

By means of the method described above for converting carbon dioxide into CO, it is possible to convert the hot carbon from the hydrocarbon converter 9 in the $CO_2$ converter 9 with warm or hot carbon dioxide from the exhaust gas from industrial processes to CO without or at least without significant external energy supply. Preferably, at least 80%, specifically at least 90%, of the heat necessary to reach the conversion temperature should originate from the hydrocarbon converter 3.

Figure 2:
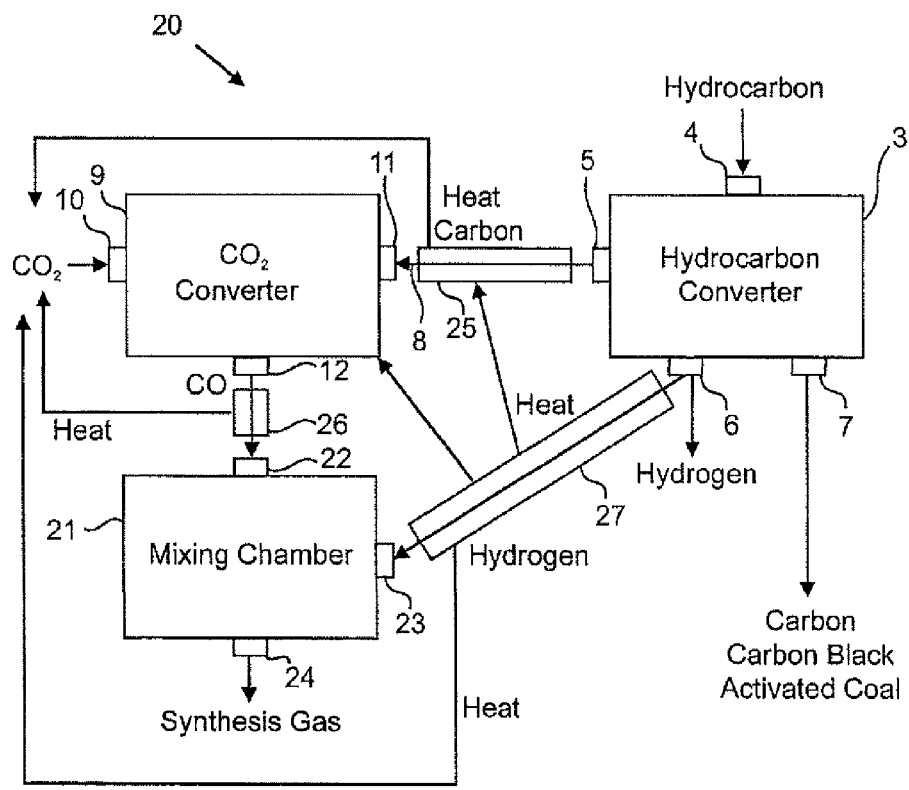
FIG. 2 is a schematic representation of a plant for generating synthesis gas.

FIG. 2 shows a plant 20 for generating synthesis gas that comprises the above described elements of plant 1 for generating carbon monoxide as well as a mixing chamber 21, the mixing chamber 21 comprising a CO inlet 22 for introducing carbon monoxide and a $H_2$ inlet 23 for introducing hydrogen as well as a synthesis gas outlet 24 for discharging synthesis gas. The CO inlet 22 is connected to the CO outlet 12 of the $CO_2$ converter 9. The $H_2$ inlet 23 of the mixing chamber 21 is connected to the $H_2$ outlet 6 of the hydrocarbon converter 3. As is obvious to the skilled person, the embodiment, which introduces a C—$H_2$ mixture into the $CO_2$ converter 9 through the carbon outlet 5 automatically generates a synthesis gas having a mixing ratio of CO—$H_2$ of about 1:1. In such a case, the mixing chamber 21 may not be present, or the mixing chamber 21 may be used to produce a different mixing ratio.

The mixing chamber 21 may be any suitable apparatus for mixing gases and, in a simple case, the mixing chamber 21 may be in the form of a pipe having suitable inlets and an outlet. By means of the mixing chamber 21 and specifically by means of controlling/regulating (open/closed loop) the amount of (additional) hydrogen introduced through the $H_2$ inlet 23 of the mixing unit 21, the mixture of the synthesis gas at the synthesis gas outlet 24 may be influenced such that a composition can be achieved, which is suitable for subsequent processes.

For many processes, for instance the Fischer-Tropsch synthesis, the ratio of hydrogen to CO should be high. By means of the mixing chamber 21, any desired ratio of hydrogen to CO may be achieved at the synthesis gas outlet 24. It is considered that only a portion of the CO and/or part of the hydrogen is introduced into the mixing chamber 21, whereas those portions of CO and hydrogen that are not introduced into the mixing chamber are each discharged from the process as pure gases. Therefore, it is for instance possible, a) to discharge only CO, b) to discharge only hydrogen, c) to discharge a synthesis gas mixture of CO and hydrogen or d) to discharge a stream of CO, a stream of hydrogen and a stream of a synthesis gas mixture (CO+hydrogen).

Furthermore, the plant 20 for generating synthesis gas shown in FIG. 2 comprises a first heat exchange unit 25, a second heat exchange unit 26 and a third heat exchange unit 27. The first heat exchanger unit 25 is in thermally conductive contact with the connection 8 between the hydrocarbon converter 3 and the $CO_2$ converter 9 and is adapted to, if necessary, extract surplus heat not required to reach the conversion temperature in the $CO_2$ converter 9 from the connection or to introduce heat from other areas of the plant, if necessary.

The second heat exchanger unit 26 is in thermally conductive contact with the connection between the $CO_2$ converter 9 and the mixing chamber 21 and is adapted to extract surplus heat from the connection and thus to extract surplus heat contained in the hot CO. This surplus heat may be used e.g. to preheat the $CO_2$ that is introduced into the $CO_2$ converter 9. For this heat transfer a so-called counter flow heat exchanger unit as known in the art would be particularly suitable.

The third heat exchanger unit 27 is in thermally conductive contact with the connection between the hydrocarbon converter 3 and the mixing chamber 21 and is adapted to extract surplus heat from the connection and thus from the hot hydrogen contained therein. The heat extracted at one of the first, second or third heat exchanger units may be used to heat other areas of the plant, specifically to keep the $CO_2$ converter warm or to preheat the $CO_2$ that is introduced into the $CO_2$ converter. A portion of the heat may be converted into electricity, for instance by a steam generator and a steam turbine or by another suitable apparatus.

The operation of plant 20 for generating synthesis gas is, with respect to the operation of the hydrocarbon converter 3 and the CO2 converter 9, similar to the above described operation of plant 1 according to FIG. 1. In plant 20 for generating synthesis gas, a desired mixing ratio of hydrogen to CO is set in the mixing chamber and is discharged through the synthesis gas outlet 24 of the mixing chamber, depending on the desired composition of the synthesis gas. Preferably, but not necessarily, the hydrogen is provided by the hydrocarbon converter 3, as was described. Other hydrogen sources may be considered, particularly a second hydrocarbon converter 3, particularly a low temperature hydrocarbon converter. If not the entire available amount of CO and/or the entire available amount of $H_2$ are used, those parts of the gases CO and $H_2$ that are not mixed in the mixing chamber may be processed separately.

Figure 3:
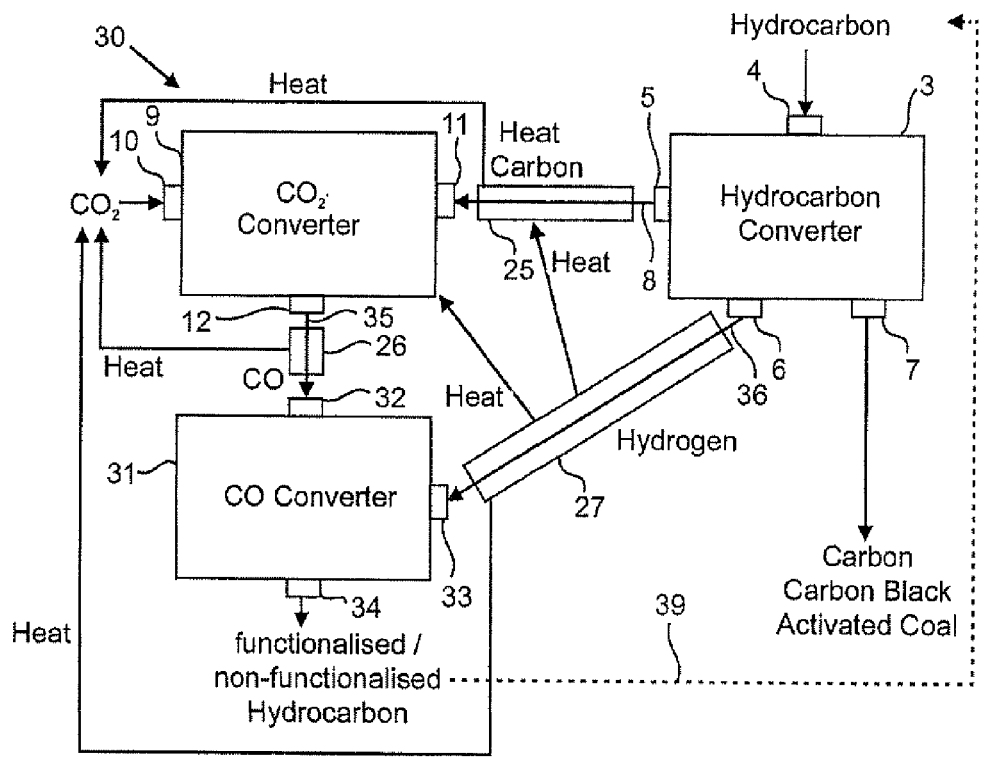
FIG. 3 is a schematic representation of a plant for generating functionalised and/or non-functionalised hydrocarbon.

FIG. 3 shows a plant 30 for generating synthetic functionalised and/or non-functionalised hydrocarbons that comprises a plant 1 for converting carbon dioxide into carbon monoxide (as shown in FIG. 1) and a CO converter 31. Those parts of the plant corresponding to plant 1 are not explained in detail in order to avoid repetitions. The CO converter 31 is located downstream from the $CO_2$ converter 9 and comprises a CO inlet 32 for introducing CO, a $H_2$ inlet 33 for introducing hydrogen and a hydrocarbon outlet 34 for discharging synthetic functionalised and/or non-functionalised hydrocarbons. The CO inlet 32 of the CO converter 31 is connected to the CO outlet 12 of the CO2 converter 9 by means of the CO connection 35. The $H_2$ inlet 33 of the CO converter 31 is connected to the $H_2$ outlet 6 of the hydrocarbon converter 3 by means of the $H_2$ connection 36.

The plant 30 for generating hydrocarbons optionally also comprises the heat exchanger units 25, 26, 27 described in conjunction with plant 20 (FIG. 2), wherein all of these operate in the above described way (see description to FIG. 2).

The CO converter 31 may be any CO converter for generating synthetic functionalised and/or non-functionalised hydrocarbons. In the embodiment shown in FIG. 3, the CO converter is preferably a Fischer-Tropsch converter, a Bergius-Pier converter or a Pier converter with a suitable catalyst and a control unit for temperature and/or pressure.

In one embodiment, the CO converter 31 comprises a Fischer-Tropsch converter. A Fischer-Tropsch converter catalytically converts a synthesis gas into hydrocarbons and water. Several embodiments of Fischer-Tropsch reactors and Fischer-Tropsch processes are known to the person skilled in the art and are not explained in detail. The main reaction equations are as follows:

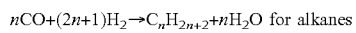

$n\text{CO}+(2n+1)\text{H}_2 \rightarrow \text{C}_n\text{H}_{2n+2}+n\text{H}_2\text{O}$ for alkanes

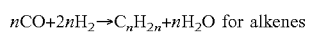

$n\text{CO}+2n\text{H}_2 \rightarrow \text{C}_n\text{H}_{2n}+n\text{H}_2\text{O}$ for alkenes

$n\text{CO}+2n\text{H}_2 \rightarrow \text{C}_n\text{H}_{2n+1}\text{OH}+(n-1)\text{H}_2\text{O}$ for alcohols The Fischer-Tropsch processes may be carried out as high temperature processes or as low temperature processes, wherein the process temperatures are usually in the range of 200 to 400° C. Known variants of the Fischer-Tropsch process are, among others, the Hochlast synthesis, the Synthol synthesis and the SMDS process of Shell (SMDS=Shell Middle Distillate Synthesis). A Fischer-Tropsch converter typically produces a hydrocarbon compound of wet gases (propane, butane), petrol, kerosene, soft paraffin, hard paraffin, methanol, methane, Diesel fuel or a mixture of several of these. It is known to the person skilled in the art that the Fischer-Tropsch synthesis is exothermic. The heat of reaction from the Fischer-Tropsch process may be used e.g. by means of a heat exchanger unit (not shown in the figures) to preheat the $CO_2$. As an example, a two-step preheating process for the $CO_2$ to be introduced into the $CO_2$ converter 9 is considered, wherein a first preheating step is realised with the surplus heat of the CO converter 31 (in the embodiment of a Fischer-Tropsch converter) and subsequently a step of further heating of the $CO_2$ by means of the heat from one or more of the heat exchanger units 25, 26, 27.

In an alternative embodiment, the CO converter 31 comprises a Bergius-Pier converter or a combination of a Pier converter with a MtL converter (MtL=Methanol-to-Liquid).

In a Bergius-Pier reactor, the Bergius-Pier process, which is well known to a person skilled in the art, is carried out, wherein hydrocarbons are generated by hydrogenation of carbon with hydrogen in an exothermic chemical reaction. The range of products from the Bergius-Pier process depends on the reaction conditions and control of the reaction process. Mainly liquid products are obtained, which may be used as transportation fuels, for instance heavy and medium oils. Known variants of the Bergius-Pier process are for instance the Konsol process and the H-Coal process.

In the above mentioned combination of a Pier converter with a MtL converter, at first synthesis gas is converted into methanol according to the Pier process. The MtL converter is a converter that converts methanol into petrol. A widespread process is the MtL process of ExxonMobil respectively Esso. Starting material of the MtL converter is typically methanol, for instance from the Pier converter. The exit product generated by the MtL converter typically is petrol, which is suitable for the operation of an Otto engine.

It may be summarized that the CO converter 31, regardless of the operating principles explained above, generates synthetic functionalised and/or non-functionalised hydrocarbons from CO and $H_2$ as its output or end products. By means of a heat exchanger unit, the process heat produced during the exothermic conversion in the CO converter 31, may be used to heat different sections of the plant or to generate electricity in order to increase the efficiency of the described plant.

As far as a mixture of hydrocarbons, which cannot be further processed directly or sold profitably as a final product after separation and specification, is obtained as exit products of the CO converter 31, these hydrocarbons, for instance methane or short-chain paraffins, may be recycled into the process described above. For this purpose, the plant 30 comprises a recycle connection 39, which can direct a portion of the synthetically generated hydrocarbons back to the hydrocarbon inlet 4 of the hydrocarbon converter 3. Depending on the composition of the recycled, synthetically generated hydrocarbons, a treatment or separation step of unsuitable hydrocarbons is carried out prior to introducing the unsuitable hydrocarbons into the hydrocarbon inlet 4.

Figure 4:
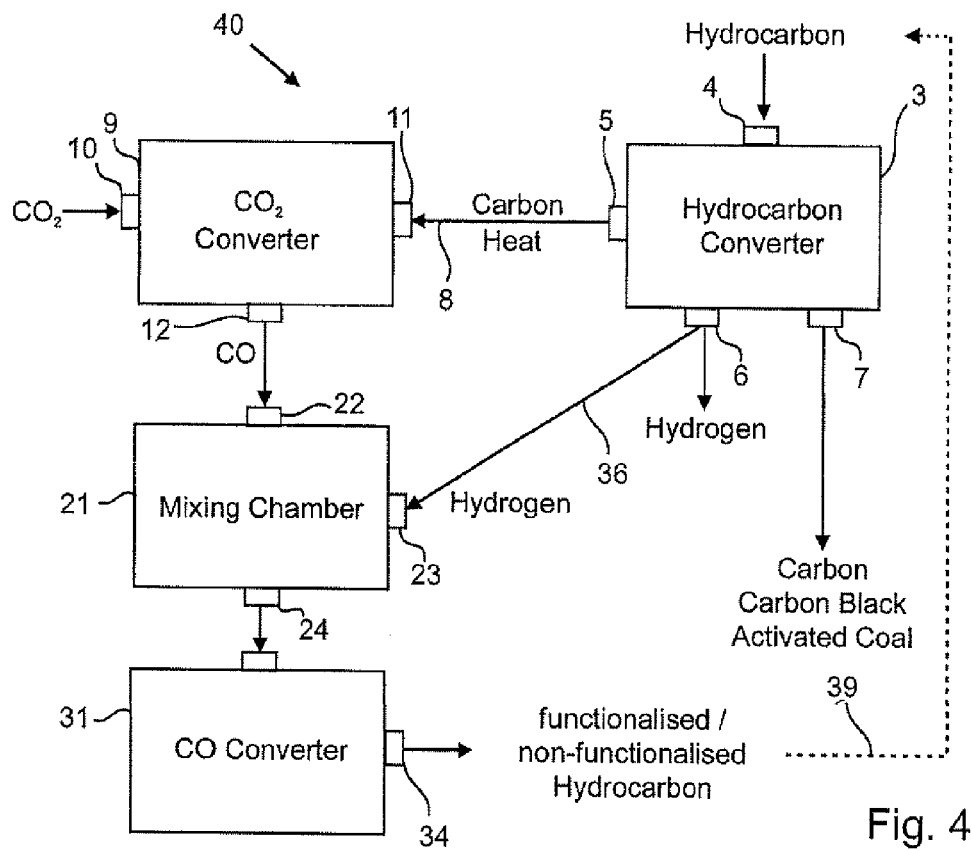
FIG. 4 is a schematic representation of another plant for generating functionalised and/or non-functionalised hydrocarbons according to another embodiment.

FIG. 4 shows a further embodiment of a plant 40 for generating synthetic functionalised and/or non-functionalised hydrocarbons. The plant 40 comprises the above described plant 20 for generating a synthesis gas as well as a CO converter 31 as described above with reference to the embodiment in FIG. 3. The synthesis gas outlet 24 of the mixing chamber 21 is connected to the CO converter 31. The mixing chamber 21 is set in such a way that it provides a synthesis gas specifically adapted to the needs of the CO converter 31 in use at the synthesis gas outlet 24. The other elements of plant 40 are the same as described above and the operation of the individual elements essentially takes place in the way described above.

It is considered that, depending on the size of the plant, a plurality of hydrocarbon converters are operated in parallel in order to provide the desired conversion capacity. As mentioned above, the hydrocarbon converters may be constructed as high temperature hydrocarbon converters and/or as low temperature hydrocarbon converters. A high temperature hydrocarbon converter operates at temperatures above 1000° C. and a low temperature hydrocarbon converter operates at temperatures between 200 and 1000° C., wherein an additional source of energy, for instance a microwave unit, may be provided in order to achieve decomposition of the hydrocarbon into carbon and hydrogen.

Figure 5:
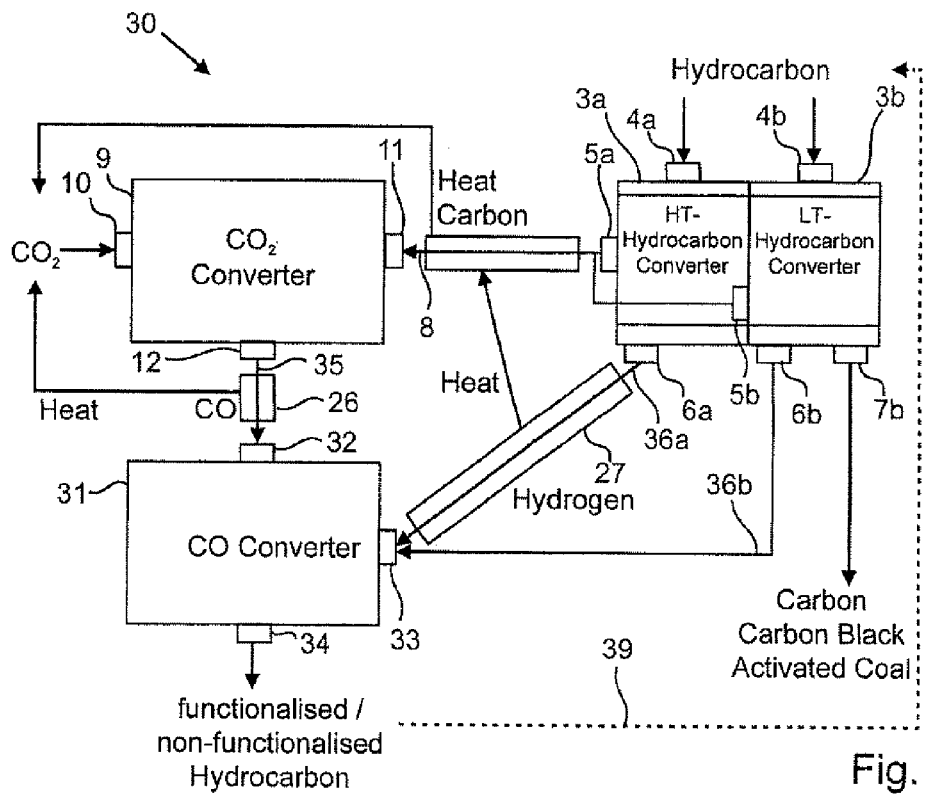
FIG. 5 is a schematic representation of a plant for generating functionalised and/or non-functionalised hydrocarbons according to another embodiment.

As an example for a plant with a plurality of parallel operated hydrocarbon converters, FIG. 5 shows a further embodiment of plant 30 for generating synthetic functionalised and/or non-functionalised hydrocarbons. FIG. 5 uses the same reference numerals as in earlier embodiments, as far as the same or similar elements are described. In the embodiment shown in FIG. 5, a combination of a high temperature hydrocarbon converter 3a and a low temperature hydrocarbon converter 3b is shown instead of a single hydrocarbon converter 3.

The high temperature hydrocarbon converter 3a comprises a hydrocarbon inlet 4a, a first outlet 5a to discharge carbon and a second outlet 6a to discharge hydrogen. Again, a single outlet 5a may be provided for a mixture (particularly an aerosol) of carbon and hydrogen. The outlet 5a is connected to the inlet 11 of the CO2 converter 9 by a connection 8. The optional outlet 6a of the high temperature hydrocarbon converter 3a is connected to the H2 inlet 33 of the CO converter 31. The high temperature hydrocarbon converter 3a may optionally comprise a further outlet for carbon (not shown in FIG. 5).

The low temperature hydrocarbon converter 3b comprises a process chamber having a hydrocarbon inlet 4b, a first outlet 5b to divert carbon, a second outlet 6b for discharging hydrogen and an optional third outlet 7b for discharging carbon. Preferably, the low temperature hydrocarbon converter 3b comprises a separation unit for separating hydrogen and carbon after decomposition and for directing the hydrogen and carbon to their respective outlets. The first outlet 5b is optionally connected to inlet 11 of the $CO_2$ converter 9 via connection 8, but may also be connected to a carbon collection unit. The outlet 6b of the low temperature hydrocarbon converter 3b is connected to the $H_2$ inlet 33 of the CO converter 31. The optional third outlet 7b is connected to a carbon collection unit from which collected carbon may be withdrawn, for instance as carbon black, activated coal or in another form.

The hydrocarbon introduced into the hydrocarbon inlet 4a and the hydrocarbon introduced into the hydrocarbon inlet 4b may be the same hydrocarbon or may be different hydrocarbons. A hydrocarbon from a first hydrocarbon source may be introduced into the hydrocarbon inlet 4a, for instance natural gas from a natural gas source. However, e.g. functionalised and/or non-functionalised, synthetically generated hydrocarbon may be introduced into the hydrocarbon inlet 4b of the low temperature hydrocarbon converter 3b, for instance via the earlier mentioned optional recycle connection 39. Because of the utilisation of several parallel operated hydrocarbon converters 3a, 3b, the plant 30 may be scaled easier, may be controlled easier, and different kinds of carbon may be produced.

Furthermore, the high temperature hydrocarbon converter 3a may for instance be used advantageously to generate "hot" carbon, preferably at a temperature over 1000° C., for the $CO_2$ conversion process in the $CO_2$ converter 9. In particular, the high temperature hydrocarbon converter 3a may operate in this case without a separation unit, since the C—$H_2$ mixture, obtained by decomposing, may be introduced directly into the $CO_2$ converter. In this case, the $CO_2$ converter 9 produces a synthesis gas having a C—$H_2$ mixing ratio of e.g. about 1:1 at the outlet.

The low temperature hydrocarbon converter 3b, however, is primarily used in order to provide additional hydrogen for the generation of a synthesis gas or a C—$H_2$ mixture having a C—$H_2$ mixing ratio of greater than 1:1, in particular greater than 1:2 in the CO converter 31. As no heat transfer from the low temperature hydrocarbon converter 3b to a subsequent process is necessary, the low temperature hydrocarbon converter 3b may advantageously be operated at temperatures below 1000° C. and preferably at the lowest possible temperature.

Thus, a portion of the carbon produced in the hydrocarbon converters 3a, 3b (preferably the portion from the high temperature hydrocarbon converter 3a) may be introduced into the $CO_2$ converter 9 during the operation of plant 30, whereas another portion (preferably the portion from the low temperature hydrocarbon converter 3b) may be discharged from the process as raw material for producing further products. Such products are for instance carbon black or industrial soot, activated coal, special kinds of carbon such as carbon discs and carbon cones etc., which is obtained as black powdery solid matter. This carbon is an important technical product, which may be used e.g. as filler in the rubber industry, as pigment soot for printing colours, inks, paints or as starting material for the generation of electrical components, for instance zinc-carbon-batteries and for the production of cathodes or anodes. Any surplus hydrogen may be discharged for the chemical industry or may be used for generating electricity (by burning), whereby the low temperature hydrocarbon converter 3b is preferably operated in such a way that it only provides the necessary additional hydrogen.

Figure 6:
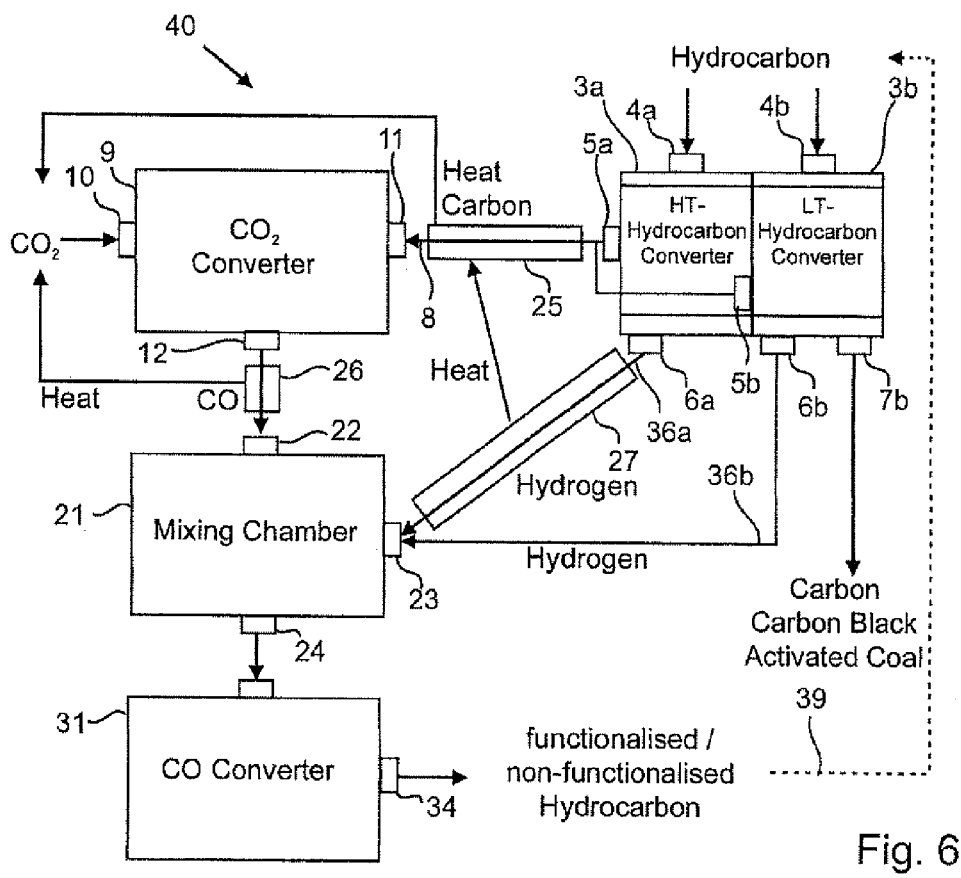
FIG. 6 is a schematic representation of a plant for generating functionalised and/or non-functionalised hydrocarbons according to another embodiment.

FIG. 6 shows an alternative embodiment of the above described plant 40 for generating synthetic functionalised and/or non-functionalised hydrocarbons, for which a plurality of parallel operated high temperature and/or low temperature hydrocarbon converters are provided as well.

The plant 40 for generating hydrocarbons shown in FIG. 6 differs from the plant 30 shown in FIG. 5 in such a way that a mixing chamber 21 is located upstream of the CO converter 31. The mixing chamber 21 mixes a synthesis gas specifically adapted to the CO converter 31 and provides the synthesis gas to the CO converter 31. The elements depicted in FIG. 6 have already been described above and work according to the principles described above. Therefore, no detailed description is given in order to avoid repetitions.

Figure 7:
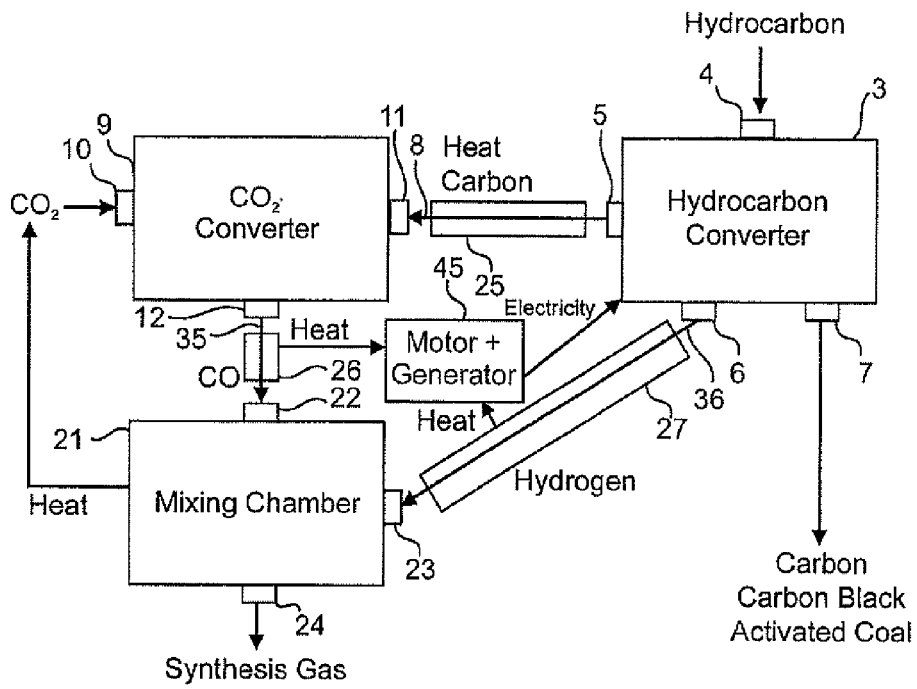
FIG. 7 is a schematic representation of a plant for generating synthesis gas according to another embodiment.
Figure 8:
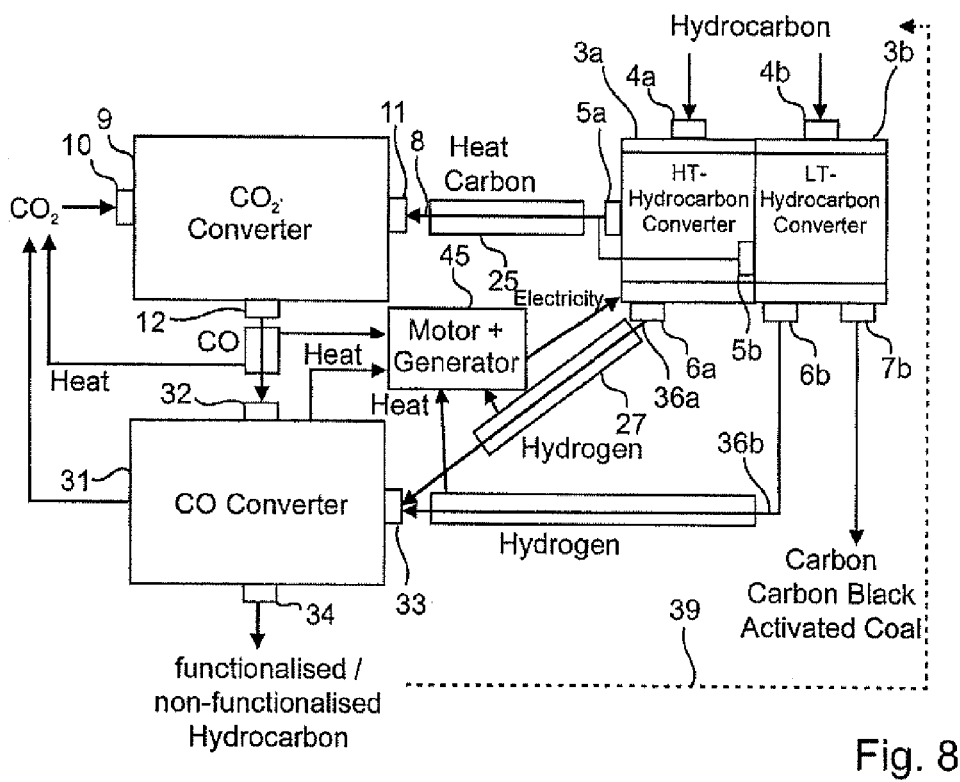
FIG. 8 is a schematic representation of a plant for generating functionalised and/or non-functionalised hydrocarbons according to another embodiment.

FIGS. 7 and 8 show embodiments of the plants 20 and 30 comprising a first heat exchanger unit 25, a second heat exchanger unit 26 and a third heat exchanger unit 27, wherein each is connected to an engine/generator device 45. The engine/generator device 45 is adapted to at least partially generate electricity from surplus heat from different sections of the plant, wherein said electricity may either be fed into the main grid or may be used to operate the plant 20, especially the hydrocarbon converter(s). Further, the engine/generator device 45 may be connected to a heat exchanger unit (not shown in FIG. 8), which dissipates the heat generated by the exothermic conversion process taking place inside the CO converter 31. Thus, on the one hand the CO converter may be cooled in a controlled and regulated way, which is advantageous for the operation of the process, and on the other hand electricity may be generated. The engine/generator device 45 may be any device that is adapted to transform heat energy into electricity, for instance a combination of a steam turbine and a generator or a piston engine and a generator.

During operation, the engine/generator device 45 transforms the surplus heat of the plant into electricity, i.e. the heat that is not necessary for $CO_2$ conversion.

The engine/generator device 45 and the heat exchanger units 25, 26 and 27 are optional elements that may be used at all plants described above. Due to the operation temperature in the respective hydrocarbon converter 3, 3a, 3b, the carbon discharged from the respective second outlets 7, 7a, 7b also contains significant amounts of heat energy. Depending on the desired temperature of the discharged carbon, a large amount of this heat energy may be dissipated by means of heat exchanger units (not shown in the figures) and the heat may be reused in the processes described herein and/or may be transformed into electricity using the engine/generator device 45.

In the plants 30 and 40 for generating synthetic functionalised and/or non-functionalised hydrocarbons, cooling of the hydrogen from the hydrocarbon converters 3, 3a, 3b and/or cooling of the CO from the $CO_2$ converter 9 is performed only as far as the temperature of the hydrocarbons and of the hydrogen does not fall below the operating temperature of the CO converter 31. The operating temperature of the CO converter 31 is usually between 200 and 400° C., depending on the chosen process.

In all plants described above, the hydrocarbon converter 3 may be a high temperature reactor operating at a temperature of more than 1000° C. (e.g. a high temperature Kvaerner reactor) or a low temperature reactor operating at a temperature between 200° C. and 1000° C. (e.g. a low temperature Kvaerner reactor). A presently tested low temperature reactor operates at temperatures between 300 and 800° C. In the case of a low temperature reactor operating at temperatures between 200 and 800° C., it is considered that the introduced carbon is preheated in the connection 8 between the hydrocarbon converter 3 and the $CO_2$ converter 9, as the $CO_2$ converter 9 operates at temperatures between 800 and 1000° C. Further, it becomes clear from FIGS. 7 and 8 that a combination between high temperature and/or low temperature converters may be used in all plants 1, 20, 30 and 40 described above.

In all plants 1, 20, 30 and 40 described above, a portion of the carbon generated in the hydrocarbon converters 3, 3a, 3b may be discharged as carbon black, as activated coal or as another raw material as long as said carbon is not converted in the $CO_2$ converter 9 of plant 1, 20, 30, 40. It shall further be noted that also a portion of the hydrogen produced in the hydrocarbon converter 3 may be directly discharged out of the process and may be sold as commodity. Further, undesired synthetic functionalised and/or non-functionalised hydrocarbons generated in the CO converter 31 may be returned and fed into the hydrocarbon inlets 4, 4a, 4b of the hydrocarbon converter 3 in all plants 30 and 40 described above.

It is considered that the $CO_2$ introduced into the $CO_2$ converter 9 is a exhaust gas from a combustion power plant or that the $CO_2$ is generated in another industrial process. Recently, emphasis is put on releasing smaller amounts of $CO_2$ into the environment, as $CO_2$ is seen as a climate pollutant. In the above mentioned exhaust gases, the $CO_2$ is mixed with other gases including, amongst others, a large amount of nitrogen from the air. With none of the above described plants 1, 20, 30, 40 is it necessary to separate the nitrogen prior to introducing the mixture of $CO_2$ and other gases into the $CO_2$ converter 9. As far as these other gases are only present in small amounts or are chemically inert (e.g. nitrogen), the operation of the $CO_2$ converter 9 is not compromised by the additional gases. A residual component of oxygen is burned in the $CO_2$ converter at the high operating temperature in presence of carbon.

Some examples follow for further clarification:

Example 1

$CO_2$ Neutral Gas Power Plant

By means of a Kvaerner reactor as the hydrocarbon converter 3, methane is decomposed into carbon and hydrogen. For each atom of carbon, two molecules of hydrogen will be obtained ($CH_4 \rightarrow C + 2H_2$). Starting from a conventional natural gas power station, for instance of the type Irsching IV, manufactured by Siemens AG, having a nominal capacity of 561 MW, the $CO_2$ contained in the exhaust gas is introduced into the $CO_2$ converter 9—about 1.5 million tons a year. The $CO_2$ from the exhaust gas of the natural gas power plant is reduced with half of the carbon discharged from the hydrocarbon converter 3. The hydrogen from the hydrocarbon converter 3 is cooled down and the dissipated heat is transformed into electricity by means of the engine/generator device 45. The $CO_2$ from the natural gas power plant is directed over hot carbon inside the $CO_2$ converter 9 and is converted into twice the amount of carbon monoxide according to the Boudouard equilibrium ($CO_2 + C \rightarrow 2CO$). The hot carbon monoxide exiting from the $CO_2$ converter 9 is cooled down, and the dissipated heat is transformed into electricity. The carbon monoxide from the $CO_2$ converter 9 (Boudouard equilibrium) and the hydrogen from the hydrocarbon converter 3 (Kvaerner process) are converted in a CO converter 31 (Fischer-Tropsch plant) to form hydrocarbons. A Heavy Paraffin Synthesis module connected to a subsequent Heavy Paraffin Conversion module from the SMDS-process (=Shell Middle Distillate Synthesis process) manufactured by Shell is preferred. The heat from the process is transformed into electricity. The nature of the resulting hydrocarbons depends on the chosen Fischer-Tropsch process and may be varied in the Shell SMDS process.

In the specific natural gas power plant (561 MW) having an efficiency of 60.4%, assuming an efficiency of 60% when transforming the process heat into electricity and assuming an efficiency of 50% when transforming dissipated heat into electricity, the process has the following parameters:

| | | |
|---|---|---|
| Consumption of methane | 2515 million S m³ $CH_4$ per year | |
| Generation of electricity | 313 MW | |
| Carbon black production | 447 000 tons per year | |
| Paraffin production | 1.0 million tons per year | |
| $CO_2$ emission | almost 0 | |
| Efficiency | natural gas power plant | 33.7% |
| | Total | 66.8% |

Example 2

Gas-to-Liquid Plant

If the plant from example 1 is operated without transforming the process heat and the dissipated heat into electricity, then no significant amount of electricity is generated. In this case, the example is a process for converting gaseous materials (carbon dioxide and methane) into liquid fuels (Otto and Diesel fuels, kerosine), i.e. a Gas-to-Liquid or GtL plant. In the present example, an additional amount of carbon is produced.

The parameters are as follows:

| | |
|---|---|
| Consumption of methane | 2515 million S m³ $CH_4$ per year |
| Generation of electricity | 0 MW |
| Carbon black production | 447 000 tons per year |
| Paraffin production | 1.0 million tons per year |
| $CO_2$ emission | almost 0 |

The invention has been explained in some detail with respect to specific embodiments and examples without being limited to these examples. In particular, the elements of the individual embodiments may be combined and/or exchanged with each other, if compatible. The skilled person will become aware of manifold modifications and deviations within the scope of the following claims. In a particularly simple embodiment of the plant for generating synthetic functionalised and/or non-functionalised hydrocarbons, the $CO_2$ converter may be designed e.g. as a simple pipe (for instance as an outlet pipe of a high temperature hydrocarbon converter not having a separation unit), wherein a $CO_2$ pipe leads to said pipe. The $CO_2$ pipe should join said pipe such that the two gas streams get well mixed. The pipe should be insulated and could be connected to a heating unit e.g. at an inlet section in order to heat up the pipe (especially at the beginning of the operation) to an operating temperature. Further downstream, the pipe could be connected to a heat exchanger unit adapted to extract surplus heat and to use this heat for heating other sectors of the plant and/or for generating electricity. Additionally, the pipe may comprise an inlet pipe for hydrogen (for instance downstream of the heat exchanger unit) so that the same pipe not only functions as a $CO_2$ converter, but also functions as a mixing chamber for generating a synthesis gas. The inlet pipe for hydrogen may originate e.g. from an outlet for hydrogen of a low temperature hydrocarbon converter (having a separation unit). In this case, an output end of the pipe, where a synthesis gas having a predetermined mixing ratio may be discharged, could end in a CO converter.

The invention claimed is:

1. A method for converting carbon dioxide $CO_2$ into carbon monoxide CO comprising the following steps:
   decomposing a hydrocarbon containing fluid into carbon and hydrogen by means of introduction of energy in a hydrocarbon converter, the energy at least partially being provided by heat, wherein the decomposing step takes place at a temperature above 1000° C. and wherein the carbon and the hydrogen have a temperature of at least 200° C. after the decomposing step;
   directing at least a portion of the carbon generated by the decomposing step from the hydrocarbon converter into a $CO_2$ converter;
   introducing $CO_2$ gas from an external $CO_2$ source into the $CO_2$ converter;
   mixing the $CO_2$ gas with at least a portion of the carbon generated by the decomposing step, wherein upon mixing the carbon with the $CO_2$ gas, the carbon obtained by the decomposing step has cooled down by no more than 50% in ° C. with respect to its temperature after the decomposing step;
   converting at least a portion of the $CO_2$ gas and the carbon obtained by the decomposing step into CO at a temperature between 800 and 1700° C.

2. The method for converting $CO_2$ into CO according to claim 1, wherein the carbon is mixed with the $CO_2$ gas at a temperature of at least 800° C.

3. The method for converting $CO_2$ into CO according to claim 1, wherein the heat required to reach the temperature of between 800 and 1700° C. for the $CO_2$ conversion originates essentially completely from the heat that is provided for decomposing the hydrocarbon containing fluid.

4. The method for converting $CO_2$ into CO according to claim 1, wherein the carbon obtained by the decomposing step and the hydrogen obtained by the decomposing step are jointly mixed with the $CO_2$ gas.

5. The method for converting $CO_2$ into CO according to claim 1, wherein the carbon obtained by the decomposing step is separated from the hydrogen obtained by the decomposing step prior to the step of mixing the carbon with the $CO_2$ gas.

6. The method for converting $CO_2$ into CO according to claim 1, wherein at least a portion of the heat of at least one of a portion of the carbon obtained by the decomposing step and a portion of the hydrogen obtained by the decomposing step is used to one of heating the $CO_2$ gas prior to mixing the $CO_2$ gas with carbon and heating the process chamber, in which the $CO_2$ gas is mixed with the carbon.

7. The method for converting $CO_2$ into CO according to claim 1, wherein the CO has a temperature of 800 to 1700° C. after conversion, and wherein at least a portion of the heat of the CO is used to preheat the $CO_2$ gas prior to mixing with the carbon.

8. The method for converting $CO_2$ to CO according to claim 1, wherein at least a portion of the heat of at least one of a portion of the carbon obtained by the decomposing step and a portion of the hydrogen obtained by the decomposing step and a portion of the $CO_2$, after conversion to CO, is used for generating electricity, wherein the electricity may particularly be provided as energy carrier for introducing energy for decomposing the hydrocarbon containing fluid.

9. The method for converting $CO_2$ into CO according to claim 1, wherein the energy is primarily introduced by means of a plasma.

10. The method for converting $CO_2$ into CO according to claim 1, wherein the decomposing step is performed in a Kvaerner reactor.

11. A method for generating a synthesis gas, wherein $CO_2$ is first converted into CO according to the method of claim 1; and wherein hydrogen is mixed with the CO subsequently.

12. The method for generating a synthesis gas according to claim 11, wherein additional hydrogen is added to the synthesis gas, and wherein the additional hydrogen is generated by decomposing a hydrocarbon containing fluid into carbon and hydrogen by introduction of energy that is at least partially provided by heat.

13. The method for generating a synthesis gas according to claim 12, wherein at least a portion of the additional hydrogen is generated by decomposing a hydrocarbon containing fluid at a temperature below 1000° C. by means of a microwave plasma.

14. The method for generating a synthesis gas according to claim 11, wherein the ratio of CO to hydrogen of the synthesis gas has a value of 1:1 to 1:3.

15. A method for generating synthetic functionalised and/or non-functionalised hydrocarbons, wherein at first a synthesis gas is generated according to the method of claim 11, and wherein the synthesis gas is brought into contact with a suitable catalyst in order to cause conversion of the synthesis gas into at least one of synthetic functionalised and synthetic non-functionalised hydrocarbons, wherein the temperature of at least one of the catalyst and the synthesis gas is open-loop controlled or close-loop regulated to a predetermined range of temperature.

16. The method for generating synthetic functionalised and/or non-functionalised hydrocarbons according to claim 15, wherein the conversion of the synthesis gas is carried out by means of one of the following: a Fischer-Tropsch process, a SMDS process, a Bergius-Pier process, a Pier process or a combination of a Pier process and a MtL process.

17. The method according to claim 1, wherein the hydrocarbon containing fluid to be decomposed is natural gas, methane, wet gases, heavy oil or a mixture thereof.

* * * * *